United States Patent [19]

Hauck et al.

[11] 4,166,183
[45] Aug. 28, 1979

[54] TRICYCLIC CYCLITOLAMINES

[75] Inventors: Frederic P. Hauck, Bridgewater; Joyce Reid, Dayton, both of N.J.

[73] Assignee: E. R. Squibb & Sons, Inc., Princeton, N.J.

[21] Appl. No.: 889,471

[22] Filed: Mar. 23, 1978

[51] Int. Cl.² .................. C07D 215/20; C07D 217/02
[52] U.S. Cl. .................................... 546/101; 546/147; 424/258
[58] Field of Search ...................... 260/287 CF, 289 C

[56] References Cited

U.S. PATENT DOCUMENTS

| | | | |
|---|---|---|---|
| 3,894,031 | 7/1975 | Hauck et al. | 260/293.56 |
| 3,971,823 | 7/1976 | Hauck et al. | 260/490 |
| 4,065,485 | 12/1977 | Hauck et al. | 260/465 P |

OTHER PUBLICATIONS

Schiffman et al., "J. Amer. Chem. Soc.", (1958), vol. 80, p. 6663.

*Primary Examiner*—David Wheeler
*Attorney, Agent, or Firm*—Lawrence S. Levinson; Donald J. Barrack

[57] ABSTRACT

Compounds having the formula

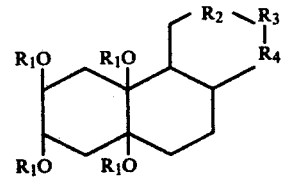

wherein $R_1$ is alkanoyl; and one of $R_2$, $R_3$ and $R_4$ is

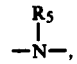

wherein $R_5$ is alkyl, and the other groups are $-CH_2-$; have useful hypotensive activity.

9 Claims, No Drawings

TRICYCLIC CYCLITOLAMINES

BACKGROUND OF THE INVENTION

Various cyclitol derivatives are disclosed in the prior art as having hypotensive activity. U.S. Pat. No. 3,894,031, issued July 8, 1975, discloses, inter alia, compounds having the formula

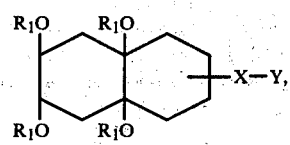

wherein $R_1$ is as defined hereinafter, X is a bivalent aliphatic radical and Y is an amino group, certain substituted amino groups, or certain nitrogen containing heterocyclic groups. Compounds having the above formula wherein Y represents certain substituted amino groups not disclosed in the above referenced patent are disclosed in U.S. Pat. Nos. 3,971,823, issued July 27, 1976 and 4,065,485 issued Dec. 27, 1977.

SUMMARY OF THE INVENTION

Compounds having the formula

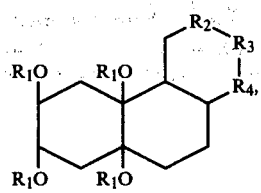

have useful hypotensive activity. In formula I, and throughout the specification, the symbols are as defined below:

$R_1$ is alkanoyl; and
one of $R_2$, $R_3$ and $R_4$ is

wherein $R_5$ is alkyl of 1 to 6 carbon atoms, and the other groups are —CH$_2$—. The preferred $$-\overset{R_5}{\underset{|}{N}}-$$

group is

The term "alkanoyl", as used throughout the specification, refers to groups having 2 to 7 carbon atoms; acetyl is the preferred group.

DETAILED DESCRIPTION OF THE INVENTION

The products of formula I can be prepared from compounds having the formula

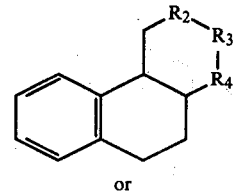

or

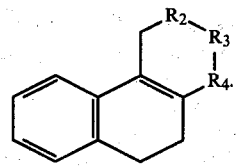

Compounds of formulas II and III are known in the art. An exemplary disclosure can be found in *Journal of the American Chemical Society*, 80, 6663 (1958) which discloses the preparation of the compound of formula III wherein $R_4$ is

and $R_2$ and $R_3$ are methylene. *Canadian Journal of Chemistry*, 52, 2316 (1974) discloses the preparation of compounds of formula III wherein $R_3$ is

and $R_2$ and $R_4$ are methylene. *Tetrahedron Letters*, No. 12, 1001 (1974) discloses the preparation of compounds of formula II wherein $R_2$ is

and $R_3$ and $R_4$ are methylene.

A compound of either formula II or formula III can be subjected to a Birch reduction to yield an intermediate having the formula

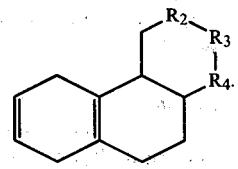

The well-known Birch reduction comprises the reduction of an aromatic compound using ammonia and a metal. For the reduction of an aromatic compound of formula II or III it has been found effective to utilize lithium ribbon as the metal.

Oxidation of a diene of formula IV yields a compound having the formula

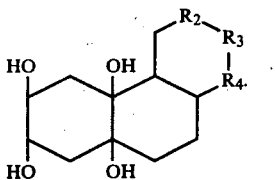

The oxidation can be accomplished by treating a diene of formula IV with formic acid and hydrogen peroxide followed by basic hydrolysis. The tetrols of formula V are novel intermediates, and as such, they constitute an integral part of this invention.

A tetrol intermediate of formula V can be converted into the corresponding product of formula I by reaction with the appropriate acid anhydride (($R_1CO)_2O$) in the presence of an acid catalyst such as perchloric acid.

The compounds of formula I contain six asymmetric centers; i.e., the four carbon atoms to which are joined the $R_1O$—groups and the two carbon atoms fusing the nitrogen containing ring to the adjacent ring. In the preferred embodiment of this invention, the four $R_1O$—groups will be axially oriented and the fusion of the nitrogen containing ring and the adjacent ring is, therefore, trans. The fusion of the nitrogen ring and the adjacent ring, while preferably trans, may be cis (two forms) or trans. The compounds exist as racemic mixtures and may be separated into their optical isomers. To illustrate the stereochemistry of the ring fusion the following configurations are shown for the benzo[f]quinoline series:

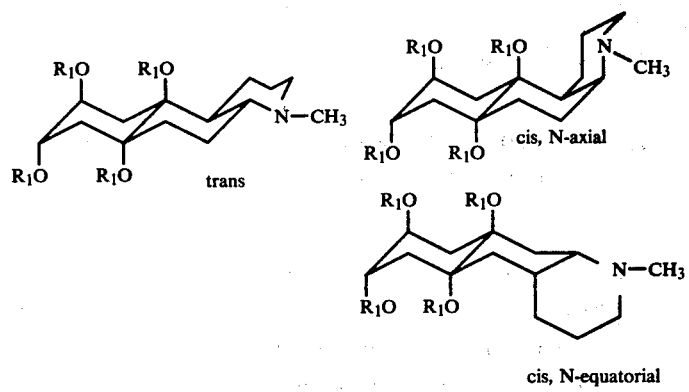

The particular stereochemistry of the ring fusion obtained in any given compound is determined: (i) by the stereochemistry of the precursor, if a precursor of formula II is used, or (ii) if a precursor of formula III is used, by the Birch reduction, which yields (on subsequent oxidation) a separable mixture of tetrols (formula V).

The compounds of formula I are useful for the treatment of hypertension in mammals. For this purpose, they can be administered in daily doses of from 5 to 50 milligrams per kilogram of body weight; preferably about 5 to 25 milligrams per kilogram of body weight can be administered in single or divided doses.

The compounds of the present invention can be administered orally, for example, with an inert diluent or with an assimilable edible carrier, or they can be enclosed in hard or soft gelatin capsules, or they can be compressed into tablets, or they can be incorporated directly with the food of the diet. For oral therapeutic administration, the active compounds of this invention can be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations can, of course, by varied and can conveniently be between about 5% to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

EXAMPLE 1

4a,9,10a-cis-Tetradecahydro-4-methylbenzo[f]-quinoline-6a,8,9,10a-tetrol, tetraacetate ester (A)

1,2,3,4,4a,5,6,7,10,10b-Decahydro-4-methylbenzo[f]quinoline

1-Methyl-1,2,3,4,7,8-hexahydrobenzo[f]-quinoline is dissolved in 200 ml of ether and added to 1.5 l of liquid ammonia. Lithium ribbon (16 g) is added portionwise over a period of 15 minutes. After stirring a few minutes, absolute ethanol is added dropwise until the color is discharged (500 ml added over a period of 2.5 hours). More ether is added and the ammonia is boiled off. While cooling in an ice bath, the mixture is diluted to about 1500 ml with water. The layers are separated and the aqueous layer is reextracted with ether. The combined organic layers are dried over potassium carbonate, filtered and the solvent is removed in vacuo leaving the title compound as a crude product.

(B)

6a,10a:8,9-trans-Tetradecahydro-4-methylbenzo[f]quinoline-6a,8,9,10a-tetrol

The crude diene prepared in Part A is added slowly to 175 ml of cold 88% formic acid. Hydrogen peroxide (60 ml of 30%) is then added dropwise over a period of 45 minutes at a temperature below 35° C. After the addition is complete the temperature is allowed to rise to 45° C. and held at 35°–45° C. for 2 hours before the mixture is left for about 16 hours in a water bath at room temperature. The mixture is taken to near dryness in vacuo. Water is added once (negative to starch-potassium iodide paper after addition) and removed in vacuo. The residue is dissolved in 175 ml of ethanol and, while cooling, is treated with a solution of 60 g of potassium hydroxide in 70 ml of water. After heating on a steam bath for 30 minutes, the mixture is diluted to 500 ml with ice water. Three ether extractions give 21.9 g of viscous material. Three ethyl acetate extractions give an additional 10.0 g of material. On standing in ethyl acetate, crystalline material is deposited (from ether extracts 8.25 g and from ethyl acetate extracts 6.9 g).

(C)
4a,9,10a-cis-Tetradecahydro-4-methylbenzo[f]-quinoliine-6a,8,9,10a-tetrol, tetraacetate ester The crystalline material from the ether extract described in Part B (3.0 g) is partially dissolved in 40 ml acetic anhydride and 2 ml of glacial acetic acid. After cooling to −40° C., 3 ml of 70% perchloric acid is added dropwise. The mixture is stored over about a 64-hour period at −12° C. After cooling to −30° C., methanol (20 ml) is added dropwise over a period of 30 minutes. The mixture is then poured into 120 ml of cold concentrated ammonium hydroxide and the product is extracted into chloroform. After drying and removal of solvent, 5.6 g of a foam remains. Hexane is added and material crystallizes which is recrystallized from ethyl acetate-hexane to give 2.6 g of the title compound, melting point 195°–203° C.

Anal. Calc'd. for $C_{22}H_{33}O_8N$: C, 60.12; H, 7.57; N, 3.19; Found: C, 60.40; H, 7.56; N, 2.99.

EXAMPLE 2

4a,9,10a,10b-cis-Tetradecahydro-2-methylbenzo[h]-isoquinoline-6a,8,9,10a-tetrol, tetraacetate ester (A)
1,2,3,4,4a,5,6,7,10,10b-Decahydro-2-methylbenzo-[h]isoquinoline 1,2,3,4,4a,5,6,10b-Octahydro-2-methylbenzo-[h]isoquinoline (11.5 g) is dissolved in 100 ml of ether and added to 700 ml of liquid ammonia. Lithium ribbon (7 g) is added portionwise over a period of 5 minutes. After stirring for a few minutes absolute ethanol is added dropwise until the color is discharged (160 ml is added over a period of 1.5 hours). More ether is added and the ammonia is boiled off. While cooling, the mixture is then diluted to 700 ml with water. The layers are separated and the aqueous layer is reextracted with ether. The combined organic layers are dried over potassiium carbonate, filtered, and the solvent is removed in vacuo leaving the crude diene product.

(B)
4a,6a,8-cis-Tetradecahydro-2-methylbenzo[h]-isoquinoline-6a,8,9,10a-tetrol

The crude diene from Part A is added to 75 ml of cold 88% formic acid. Hydrogen peroxide (30 ml of 30%) is then added dropwise over a period of 30 minutes at a temperature below 35° C. After addition is complete, the temperature is allowed to rise to 45° C. and held at 35°–45° C. for 4 hours before the mixture is left for about 16 hours in a water bath at room temperature. The mixture is then taken to near dryness in vacuo. Water is added twice (negative to starch-potassium iodide paper after second addition) and removed in vacuo. The residue is dissolved in 75 ml of absolute ethanol and, while cooling, is treated with a solution of 25 g of potassium hydroxide in 30 ml of water. After heating 30 minutes on a steam bath, the solution is diluted to about 200 ml with ice water and extracted four times with ether to give 8.2 g of a foam. The aqueous layer is then extracted three times with ethyl acetate-ethanol (10:1) to give an additional 6.7 g of foam. On standing in ethyl acetate-methanol, 1.35 g of crystalline material is deposited.

(C)
4a,9,10a,10b-cis-Tetradecahydro-2-methyl-6a,8,9,10a-benzo[H]isoquinolinetetrol, tetraacetate ester Crystalline tetrol from the ethyl acetate extract (1.3 g) in Part B is partially dissolved in 20 ml of acetic anhydride and 1 ml of glacial acetic acid. The mixture is cooled to −40° C. and 1.5 ml of 70% perchloric acid is added dropwise. The solution is stored for about 16 hours at −12° C. After cooling to −30° C., 10 ml of methanol is added dropwise over a period of 30 minutes. The mixture is then poured into 60 ml cold concentrated ammonium hydroxide. The product is extracted into chloroform, dried, and the solvent is removed in vacuo leaving a crystalline material which is recrystallized from ethyl acetate-hexane to give 1.7 g of the title compound, melting point 188°–196° C.

Anal. Calc'd. for $C_{22}H_{33}O_8N$: C, 60.12; H, 7.57; n, 3.19; Found: C, 59.83; H, 7.71; N, 2.96.

EXAMPLE 3

4a,9,10a-cis-Tetradecahydro-3-methylbenzo[f]isoquinoline-6a,8,9,10a-tetrol, tetraacetate ester Following the procedure of Example 1, but substituting 1,2,3,4,5,6-hexahydro-3-methylbenz[f]isoquinoline for 1-methyl-1,2,3-4,7,8-hexahydrobenzo[f]quinoline, yields the title compound.

What is claimed is:
1. A compound having the formula

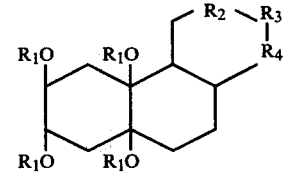

wherein $R_1$ is alkanoyl having 2 to 7 carbon atoms; and one of $R_2$, $R_3$ and $R_4$ is

wherein $R_5$ is alkyl of 1 to 6 carbon atoms, and the other groups are $-CH_2-$.

2. A compound in accordance with claim 1 wherein $R_1$ is acetyl.

3. A compound in accordance with claim 2 wherein the $R_1O$ groups are axially oriented.

4. A compound in accordance with claim 1 wherein $R_2$ is

and $R_3$ and $R_4$ are each $-CH_2-$.

5. A compound in accordance with claim 1 wherein $R_3$ is

and $R_2$ and $R_4$ are each $-CH_2-$.

6. A compound in accordance with claim 1 wherein $R_4$ is

and $R_2$ and $R_3$ are each $-CH_2-$.

7. The compound in accordance with claim 2, 4a,9,-10a-cis-tetradecahydro-4-methylbenzo[f]quinoline-6a,8,9,10a-tetrol, tetraacetate ester.

8. The compound in accordance with claim 2, 4a,9,-10a,10b-cis-tetradecahydro-2-methylbenzo[h]-isoquinoline-6a,8,9,10a-tetrol, tetraacetate ester.

9. A compound having the formula

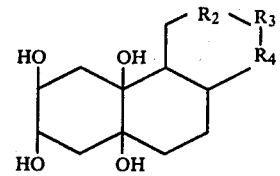

wherein one of $R_2$, $R_3$ and $R_4$ is

wherein $R_5$ is alkyl of 1 to 6 carbon atoms and the other groups are $-CH_2-$.

* * * * *

UNITED STATES PATENT OFFICE
CERTIFICATE OF CORRECTION

Patent No. 4,166,183            Dated August 28, 1979

Inventor(s) Frederic P. Hauck, et al

It is certified that error appears in the above-identified patent and that said Letters Patent are hereby corrected as shown below:

In column 1, line 30, add --I-- to the right of the structure in the "Summary of the Invention"

In column 4, line 6, delete "by" and add in its place --be--

In column 5, line 11, please correct the spelling of the word --quinoline--

In column 5, line 47, please correct the spelling of the word --potassium--

*Signed and Sealed this*

*Nineteenth* Day of *August 1980*

[SEAL]

*Attest:*

SIDNEY A. DIAMOND

*Attesting Officer*      *Commissioner of Patents and Trademarks*